United States Patent [19]

Ratnaraj et al.

[11] Patent Number: 5,686,107
[45] Date of Patent: Nov. 11, 1997

[54] CHEWABLE PHARMACEUTICAL TABLETS

[75] Inventors: Sheila Ratnaraj, Telford; William J. Reilly, Jr., New Hope, both of Pa.

[73] Assignee: FMC Corporation, Philadelphia, Pa.

[21] Appl. No.: 380,522

[22] Filed: Jan. 30, 1995

[51] Int. Cl.⁶ .................................................. A61K 9/20
[52] U.S. Cl. .................. 424/464; 424/494; 424/488; 424/489
[58] Field of Search ........................... 424/464, 494, 424/488, 489; 426/96; 260/239.1

[56] References Cited

U.S. PATENT DOCUMENTS

| | | | |
|---|---|---|---|
| 3,951,953 | 4/1976 | Khan | 260/239.1 |
| 4,952,402 | 8/1990 | Sparks et al. | 424/494 |
| 5,192,569 | 3/1993 | Mc Ginley et al. | 429/96 |

*Primary Examiner*—Thurman K. Page
*Assistant Examiner*—William E. Benston, Jr.
*Attorney, Agent, or Firm*—Mark A. Greenfield; Robert L. Andersen

[57] ABSTRACT

Formulations of chewable pharmaceutical tablets for delivery of prescription pharmaceutical actives, non-prescription pharmaceutical actives, or over-the-counter actives comprise as an excipient an aggregate of coprocessed microcrystalline cellulose and a galaotomannan. Addition of these excipients imparts improved smell, taste, texture, and mouthfeel to the finished product.

26 Claims, No Drawings

CHEWABLE PHARMACEUTICAL TABLETS

BACKGROUND OF THE INVENTION

1. Field of the Invention

The present invention relates to improved formulations of chewable tablets for the delivery of pharmaceuticals to patients. More particularly, it relates to formulations of chewable tablets having improved characteristics, resulting in greater acceptability by patients receiving pharmaceuticals in this form.

2. Description of the Related Art

In addition to the therapeutic ingredients of pharmaceutical tablets (commonly referred to as "actives"), materials inert and non-reactive with respect to the actives (commonly referred to as "excipients") are added to the tablet formulation to confer specific properties not related to the activity of the therapeutic agents. Excipients such as diluents, binders, glidants, and lubricants are added as processing aids to make the tableting operation more effective. Other excipients such as microcrystalline cellulose are also added to improve the compression of the tablets. Still other types of excipients added to pharmaceutical tablets are those which enhance or retard the rate of disintegration of the tablet in the patient, improve the taste of the tablet, (for example sweetening agents), or impart a color to the tablets. In some instances such materials will provide more than one of these benefits to the finished tablet. Although excipients are classified as inert materials, they are only inert in the sense that they are not pharmaceutical actives and do not provide a therapeutic effect in themselves, but they make delivery of the therapeutic agent in the most effective manner possible.

Chewable tablets, regardless their geometry, represent a particular form of oral dosage; they are intended to be chewed in the mouth by the patient and are not intended to be swallowed intact. Many chewable formulations are intended to be used to provide a known dosage of active to children or the people who either will refuse to swallow an intact tablet or may have difficulty doing so. Such tablets are often used to administer analgesics, antacids, antibiotics, anticonvulsants, vitamins, and laxatives, for example. In addition to the foregoing, chewable tablets have several advantages which make them the method of choice in delivering certain types of therapeutic agents to an even greater population. One such advantage is that certain types of tablets, because of the large size of the dosage, must be unusually large and, therefore, difficult to swallow. In some cases the effectiveness of the therapeutic agent is improved by the reduction in size that occurs during mastication of the tablets before swallowing. Furthermore, patient compliance with the prescribed therapy, such as antacid treatment, is enhanced by the use of smaller, more convenient tablets which may be consumed when it is inconvenient to swallow pills, for example, in the workplace. This is particularly true when the therapy would otherwise involve a liquid suspension of the therapeutic agent which would be inconvenient to transport, for example in chewable antacid tablets.

Excipients when added to chewable tablets must not only be inert in respect of the active, preferably they provide pleasant mouthfeel and/or prevent toothpacking, grittiness, and the like, without imparting any unpleasant characteristics to the tablets as they are chewed. Microcrystalline cellulose in various forms, such as products of the Pharmaceutical and Biosciences Division of FMC Corporation, Philadelphia, Pa. U.S.A. sold under the Avicel® brand, are frequently used as excipients in pharmaceutical tablets, but have not found ready acceptance in chewable tablet applications because of the astringent mouthfeel they may impart to a tablet as it is being chewed.

Aggregates of coprocessed microcrystalline cellulose and guar or locust bean gum have been fully described in U.S. Pat. No. 5,192,569, as well as the process by which these aggregates may be made and their physical and organoleptic properties. The aggregates are disclosed as being useful as fat replacements in such food applications as low-fat salad dressings and frozen dessert products. In this patent a brief mention is made of several other possible uses for these materials including controlled release agents, tableting excipients, flavor carriers, or bonding, bulking, or encapsulating agents. Except for this mention, there is no enabling disclosure directed toward their use as excipients nor suggestion that they possess unique properties that might suit them for use in pharmaceutical tablets nor any indication that they might provide extraordinary properties to a particular type of pharmaceutical tablet, for example "chewable" tablets.

SUMMARY OF THE INVENTION

An aggregate of a coprocessed microcrystalline cellulose and galactomannan gum when used as an excipient in a chewable formulation, results in chewable tablets containing pharmaceutical actives which tablets have improved mouthfeel and taste characteristics. For purposes of this invention the term "pharmaceutical" is defined as preparations including prescription drug actives as well as "over-the-counter" (OTC) actives (such as may be found in nonprescription drugs, vitamins, minerals, dietary supplements, allergy relief products, antacids, analgesics, appetite stimulants and suppressants, cold preparations, cough preparations, digestive aids, sore throat lozenges, and the like). Formulations utilizing these materials have been prepared and compared with commercial formulations containing the same actives. Uniformly, inventive formulations containing the microcrystalline cellulose-galactomannan gum aggregate (MCC-GG) excipients gave more pleasing mouthfeel and taste properties than either non-aggregated (that is, non-coprocessed) microcrystalline cellulose (MCC) excipients or the excipients currently used in the commercial formulations of the therapeutic agents. This result is surprising when compared with non-aggregated microcrystalline cellulose because of MCC's failure to find acceptance in chewable tablets, and it is particularly surprising in comparison with other commercially used excipients such as sucrose and mannitol, both of which impart sweetness and provide good mouthfeel and taste to chewable tablets. Galactomannans particularly useful for coprocessing with microcrystalline cellulose to be used as excipients according to this invention are guar gum and locust bean gum.

DETAILED DESCRIPTION OF THE INVENTION

Other than in the operating examples, or where otherwise indicated, all numbers expressing quantities of ingredients, parameters, or reaction conditions used herein are to be understood as modified in all instances by the term "about".

This invention provides formulations for chewable pharmaceutical and OTC tablets which have improved smell, taste, texture, and mouthfeel. Other characteristics which are improved by the invention are the reduction or elimination of initial dry mouthfeel, the tendency for chewable tablets to pack tooth crevices during mastication (commonly referred to as "toothpacking"), and chalky aftertaste. All, or at least some, of these unsatisfactory characteristics are present to a greater or lesser extent in the currently available chewable pharmaceutical and OTC tablets.

In a first embodiment, this invention incorporates an aggregate of microcrystalline cellulose coprocessed with a galactomannan gum (MCC-GG) into chewable tablets as an excipient which provides compressibility, improves mouthfeel, both initially and after complete mastication, and reduces or eliminates toothpacking. The amount of this coprocessed aggregate in the inventive formulations is generally 2 to 15 wt %, based on the total dry weight of the formulations. Particular types of tablet use, for example as antacids or analgesics, may have preferred narrower excipient addition ranges due to the nature of the actives; these are indicated where appropriate.

Examples of useful galactomannan gums to be coprocessed with microcrystalline cellulose include guar, locust bean, cassia, tara, or mixtures thereof, of which guar and locust bean are preferred and guar gum most preferred.

A coprocessed aggregate of microcrystalline cellulose with the galactomannans guar gum and/or locust bean gum which is used in these formulations has been fully described in U.S. Pat. No. 5,192,569, which is incorporated herein by reference. This coprocessed aggregate is prepared by thoroughly mixing an aqueous dispersion of microcrystalline cellulose and a galactomannan gum under high shear conditions at room temperature. After the high shear mixing or, alternatively homogenization, is complete, the dispersion is dried, preferably spray dried, to an aggregate powder having substantially spheroidal-shaped particles with an average size in the range 0.1–100 microns, each particle consisting essentially of an aggregate of 60–99 wt % (preferably 70–95 wt %) of microcrystalline cellulose with the balance to 100 wt % of at least one galactomannan gum.

In a second embodiment, a food grade or pharmaceutical grade non-coprocessed hydrocolloid ingredient optionally may be added in addition to the coprocessed aggregate; in order to enhance the creaminess of the masticated particles. Examples of such non-coprocessed hydrocolloids include gum acacia, a carrageenan (especially kappa-carrageenan), tragacanth gum, konjac, xanthan, and their mixtures. The non-coprocessed hydrocolloid ingredient may be present in 0.1 to 5.0 wt % (preferably 0.1 to 3 wt %, most preferably 0.1 to 1 wt %) based on the total formulation weight.

In a third embodiment, it optionally may be desirable to add maltodextrin as a dispersant and bulking agent, to any one of the other embodiments in 0.1 to 5.0 wt % (preferably 0.1 to 3 wt %, most preferably 0.1 to 1 wt %).

It is contemplated that any of the aggregate materials described in U.S. Pat. No. 5,192,569 would be useful in preparing chewable pharmaceutical tablets as described herein. Currently, at least two such products are commercially available for incorporation into chewable tablet formulations. They are 90% microcrystalline cellulose coprocessed with 10% guar gum and 85% microcrystalline cellulose coprocessed with 15% guar gum. These two coprocessed aggregates are manufactured and sold by FMC Corporation, Pharmaceutical Division, Philadelphia, Pa., U.S.A. as Novagel® RCN-10 and Novagel RCN-15, respectively. Products of microcrystalline cellulose coprocessed with locust bean gum are not commercially available primarily because of the higher cost of locust bean gum which would dramatically increase the cost of the coprocessed material. However, microcrystalline cellulose coprocessed with locust bean gum performs the same function as microcrystalline cellulose coprocessed with guar has been shown to perform.

Comparison of two formulations of chewable aspirin tablets detailed herein demonstrates that not all hydrocolloids coprocessed with microcrystalline cellulose will provide the same beneficial effect as the coprocessed microcrystalline cellulose/galactomannan gum aggregate. Formulations 17ASP (Table 7) and 19ASP (Table 8) have comparable amounts of most components, but the characterization of the taste and mouthfeel of these formulations is quite different. Formulation 19ASP is described as having an acidic taste. Formulation 17ASP, on the other hand, is described as being successively very sweet, slightly sour, slightly salty, but with smooth mouthfeel. The greatest difference between Formulations 17ASP and 19ASP is the type of coprocessed aggregate excipient that is used in each. In Formulation 17ASP this excipient is a material of this invention, and in Formulation 19ASP the excipient is Avicel® RCN-30, 70% microcrystalline cellulose coprocessed with 30% of a combination of xanthan gum and maltodextrin (neither of which is a galactomannan). The microcrystalline cellulose employed in 17 ASP and 19 ASP were essentially the same. Clearly, although a higher percentage of hydrocolloid has been coprocessed with the microcrystalline cellulose in 19 ASP, this high level of hydrocolloid is not able to overcome the acidic taste of the aspirin. This indicates that the inventive effect appears to be attributable primarily to the specific hydrocolloid coprocessed with the microcrystalline cellulose rather than the amount of such hydrocolloid.

In a fourth embodiment of this invention, a coprocessed microcrystalline cellulose aggregate is incorporated into formulations used to prepare chewable antacid tablets. The coprocessed aggregate is incorporated into these formulations in relatively small amounts, preferably from a minimum of 2 wt % to a maximum of 5 wt %, more preferably 2 to 3 wt %.

Before undertaking work to improve the currently commercially available chewable antacid tablets, an internal taste panel evaluated two of the most popular commercial brands. Brand A, which was preferred by 75% of the members of the taste panel, was shown to have the unpleasant properties of grittiness and a chalky aftertaste. However, the panel liked Brand A's smooth mouthfeel and its cooling sensation in the mouth. Brand B had more chalky aftertaste, a less smooth mouthfeel, and more grittiness than Brand A. Clearly, both of these products were deficient, making them less than fully acceptable to the panel.

Examples 1 and 2 provide formulations of chewable antacid tablets with improved properties. The directly compressible antacid powder used was obtained in formulated form from a manufacturer. It comprises aluminum and magnesium hydroxides, sugar, an artificial sweetener, sorbitol, and mannitol. The actual sources of all other ingredients used in Formulations 1AA to 15AA, except for the MCC-GG, are shown in the footnotes to Tables 1 to 3. The MCC-GG was incorporated into chewable antacid formulations detailed in these tables at a level of at least 2 wt %, and this amount can be increased by decreasing other components proportionately, excluding the compressible antacid powder, of course.

Some antacid formulations contain an agent, for example simethicone, to reduce the accumulation of gastrointestinal gas. The use of MCC-GG is shown in Example 3 to be effective in improving the properties of chewable tablets containing this ingredient in combination with an antacid. The useful level of MCC-GG as an excipient in these formulations is somewhat higher than in the antacid formulations containing only the compressible antacid powder, in the preferred range of 2.0 to 5.0 wt %, more preferably 2.0 to 4.5 wt %, most preferably 2.3 to 3.0 wt %.

In a fifth embodiment of this invention, coprocessed MCC-GG aggregate is incorporated into the formulations for chewable tablets of analgesics. Among the analgesics that may be formulated in this way are aspirin, acetaminophen, and ibuprofen. Chewable aspirin tablets currently are available in dosages intended for children and larger dosages intended for adults. Aspirin has a strong acidic taste which must be masked in order for the chewable tablet to be palatable to the patient. Accordingly, larger amounts of coprocessed MCC-GG aggregate must be incorporated into formulations of chewable aspirin tablets. The preferred amount of coprocessed microcrystalline cellulose incorporated into chewable aspirin tablets, both for children and adults, ranges from 5 to 15 wt %, more preferably 7 to 12 wt %, most preferably 8 to 10 wt %. Chewable tablets of untreated aspirin and, particularly microencapsulated aspirin, that have quite pleasing organoleptic properties can be made using MCC-GG as excipient. Examples 3–7 provide details of these formulations.

In a sixth embodiment of this invention, it is contemplated that coprocessed microcrystalline cellulose is added to the formulations used to prepare chewable vitamin tablets, for example multivitamin formulations or single vitamin supplements such as ascorbic acid or its salts (vitamin C). Vitamins are particularly common in chewable tablets intended for children, although adult chewable vitamin tablets are also available. Formulations of chewable vitamin tablets may contain among other ingredients sugars, dried fruit juices, other flavors, sorbitol and/or mannitol, and coloring agents. The incorporation of coprocessed microcrystalline cellulose into these chewable vitamin tablets makes them more palatable and, therefore, more likely to be used as dietary supplements, particularly for children. The amount of coprocessed MCC-GG aggregate which may be incorporated into these chewable vitamin tablets is 2 to 15 wt %.

In a seventh embodiment of this invention, it is contemplated that improved chewable tablets containing laxatives, for example phenolphthalein, are made more palatable by the incorporation of coprocessed MCC-GG aggregate into their formulation. The amount of coprocessed aggregate which may be incorporated into chewable laxative tablets is 2 to 15 wt %.

In an eighth embodiment of this invention, improved chewable tablets containing an antibiotic, for example amoxicillin or augmentin, may be made more palatable by the incorporation of coprocessed MCC-GG aggregate into their formulation. The amount of coprocessed aggregate which may be incorporated into chewable antibiotic tablets falls within the range of 2 to 15 wt %.

In a ninth embodiment of this invention, improved chewable tablets containing an anticonvulsant, for example, dilantin, may be made more palatable by the incorporation of coprocessed MCC-GG aggregate into their formulation. The amount of coprocessed aggregate which may be incorporated into chewable anticonvulsant tablets falls within the range of 2 to 15 wt %.

The following examples employ an aggregate of microcrystalline cellulose coprocessed with guar according to this invention. This is not intended as limiting, but rather as exemplary of an aggregate of microcrystalline cellulose coprocessed with any of the disclosed galactomannans.

EXAMPLE 1

Chewable Antacid Tablets Prepared with 90% Microcrystalline Cellulose Coprocessed with 10% Guar Gum as Excipient All ingredients identified in Part 1 of Table 1 below are combined in a twin shell blender and mixed for 10 minutes. The ingredients in Part 2 of Table 1 are then passed through a Number 30 standard screen and added to the mixture in the twin shell blender, and the total formulation is mixed until thoroughly blended, about four minutes. Tablets are made from this mixture using a 12.7 mm round die and a flat-faced, beveled-edge punch. Each tablet weighs approximately 0.670–0.680 gram and has a hardness of 5.0–6.0 Kp.

TABLE 1

| Formulation | 1AA (grams) | 2AA (grams) | 3AA (grams) | 4AA (grams) | 5AA (grams) |
|---|---|---|---|---|---|
| Ingredients Part 1 | | | | | |
| Antacid powder[a] | 167.90 | 167.90 | 167.90 | 167.90 | 167.90 |
| Mannitol | 8.01 | 8.01 | 8.01 | 8.01 | 8.01 |
| MCC-GG[b] | | 3.20 | 3.20 | 3.20 | 3.20 |
| Sucrose NF[c] | 9.06 | 9.06 | | | |
| Sucrose NF[d] | 9.06 | 9.06 | 9.06 | 18.12 | |
| Sucrose HF[e] | | | 9.06 | | 18.12 |
| Peppermint flavor[f] | 0.60 | 0.60 | 0.60 | 0.60 | 0.60 |
| Vanilla flavor[f] | 0.15 | 0.15 | 0.15 | 0.15 | 0.15 |
| Ingredients Part 2 | | | | | |
| Talc | 4.16 | | | | |
| Magnesium stearate | 1.04 | 2.0 | 2.0 | 2.0 | 2.0 |

[a]A directly compressible antacid powder formulation
[b]Novagel® RCN-10, a product of FMC Corporation, Philadelphia PA, U.S.A.
[c]Baker's special sugar, Domino Sugar Corporation
[d]Fruit sugar, Domino Sugar Corporation
[e]Crystal sugar, Domino Sugar Corporation
[f]Bush, Boake and Allen, subsidiary of Union Camp Corporation Formulation 1AA is described as being dry, but having a pasty feeling and causing toothpacking. Formulation 2AA also has the same characteristics as Formulation 1AA, except the pasty feeling is not present.

EXAMPLE 2

Chewable Antacid Tablets Prepared with 85% Microcrystalline Cellulose Coprocessed with 15% Guar Gum as Excipient The same procedure is used to mix the ingredients for the formulations shown in Table 2 as in Example 1. Tablets are also prepared in the same manner and have the same properties as those shown in Example 1.

TABLE 2

| Formulation | 6AA (grams) | 7AA (grams) | 8AA (grams) | 9AA (grams) | 10AA (grams) |
|---|---|---|---|---|---|
| Ingredients Part 1 | | | | | |
| Antacid powder[a] | 167.90 | 167.90 | 167.90 | 167.90 | 167.90 |
| Mannitol | 4.20[b] | 4.20[b] | 3.82[b] | 2.82[b] | 8.01[c] |
| Xylitol | | | 2.00 | | |
| MCC-GG[d] | 4.00 | 4.00 | 4.00 | 4.00 | 3.20 |
| Sucrose NF[e] | | | | | 9.06 |
| Sucrose NF[f] | 20.12 | 20.12 | 20.12 | 20.12 | 9.06 |
| Peppermint flavor[g] | 1.00 | 1.00 | 1.00 | 1.00 | 0.60 |
| Vanilla flavor[g] | 0.15 | 0.15 | 0.15 | 0.15 | 0.15 |
| Ac-Di-Sol®[h] | | | 1.0 | | |
| Ingredients Part 2 | | | | | |
| Talc | 2.0 | | | | |
| Magnesium stearate | | 2.0 | 2.0 | 2.0 | 2.0 |

[a]A directly compressible antacid powder formulation
[b]Granular mannitol
[c]Mannitol USP
[d]Novagel® RCN-15, [a product of FMC Corp., Philadelphia PA, U.S.A.]

TABLE 2-continued

| Formulation | 6AA (grams) | 7AA (grams) | 8AA (grams) | 9AA (grams) | 10AA (grams) |
|---|---|---|---|---|---|

[a]Baker's special sugar, Domino Sugar Corporation
[f]Fruit sugar, Domino Sugar Corporation
[g]Bush, Boake and Allen, subsidiary of Union Camp Corporation
[h]Brand of crosslinked carboxymethylcellulose sodium, [a product of FMC Corp., Philadelphia PA, U.S.A.]

Formulation 6AA is described as having very good taste and mouthfeel, but talc is an insufficient lubricant to compress the tablets easily; and some of the formulation sticks to the punch. Formulation 7AA corrects the sticking problem by substituting magnesium stearate for the talc. Formulation 10AA is the least satisfactory of the formulations reported in Table 2 and is described as being dry and toothpacking, but not as gritty as the commercial antacids.

EXAMPLE 3

Chewable Antacid Tablets Containing Simethicone (Dimethyl Polysiloxane) Prepared with 85% Microcrystalline Cellulose Coprocessed with 15% Guar Gum as Excipient The same procedure is used to mix the ingredients for the formulations shown in Table 3 as in Example 1. Tablets are also prepared in the same manner except that each tablet weighs approximately 1.20–1.25 grams and has a hardness of 6.0–8.0 Kp.

TABLE 3

| Formulation | 11AA (grams) | 12AA (grams) | 13AA (grams) | 14AA (grams) | 15AA (grams) |
|---|---|---|---|---|---|
| Ingredients Part 1 | | | | | |
| Antacid powder[a] | 93.41 | 93.41 | 93.41 | 93.41 | 93.41 |
| Mannitol | 4.46[b] | | 4.46[b] | 4.46[c] | 1.64[c] |
| Starch, NF[d] | 1.32 | | | | |
| MCC-GG[e] | | 8.10 | 3.64 | 3.64 | 4.82 |
| Mint flavor[f] | 0.38 | 0.38 | 0.38 | 0.38 | 0.80 |
| Cream flavor[f] | 0.03 | 0.03 | 0.03 | 0.03 | 0.03 |
| Vanilla flavor[f] | 0.12 | 0.12 | 0.12 | 0.12 | 0.12 |
| Ac-Di-Sol ®[g] | | | | | 1.00 |
| Simethicone gran. | 95.48 | 95.48 | 95.48 | 95.48 | 95.48 |
| Ingredients Part 2 | | | | | |
| Talc | 2.32 | | | | |
| Magnesium stearate | 2.48 | 2.48 | 2.48 | 2.48 | 2.48 |

[a]A directly compressible antacid powder formulation
[b]Mannitol USP
[c]Granular mannitol
[d]STA-RX ® pregelatinized starch, Colorcon Corp.
[e]Novagel ® RCN-15, a product of FMC Corp.
[f]Bush, Boake and Allen, subsidiary of Union Camp Corporation
[g]Brand of crosslinked carboxymethylcellulose sodium, a product of FMC Corp.

Formulation 15AA is characterized as being very palatable.

EXAMPLE 4

Chewable Aspirin Tablets Prepared with 90% Microcrystalline Cellulose Coprocessed with 10% Guar Gum as Excipient All ingredients listed in Table 4 except magnesium stearate are placed in a twin shell blender and mixed for ten minutes. The magnesium stearate is then added and mixing is continued for an additional three minutes. Tablets weighing approximately 1.000 gram are prepared by compressing the mixture on a Stokes press using a 15.8 mm round die and a flat-faced, beveled-edge punch. The hardness of the finished tablets ranges from 6–8 Kp.

TABLE 4

| Formulation | 1ASP (grams) | 2ASP (grams) | 3ASP (grams) |
|---|---|---|---|
| Aspirin[a] | 81.25 | 65.0 | 3.200 |
| Mannitol | 134.00[b] | 82.12[c] | 4.904[c] |
| Xylitol | 9.75 | | |
| MCC-GG[d] | 20.00 | 16.0 | 0.920 |
| Compressible sugar[e] | | 33.88 | |
| Flavoring agent[f] | 2.50 | 2.0 | 0.046 |
| Ac-Di-Sol ®[g] | 1.25 | | 0.046 |
| Magnesium stearate | 1.25 | 1.0 | 0.092 |

[a]Aspirin powder, Dow Chemical USA
[b]Granular mannitol
[c]Mannitol USP
[d]Novagel ® RCN-10, a product of FMC Corp.
[e]Di-Pac ®, a compressible sugar consisting of 97% sucrose and 3% maltodextrin, Amstar Sugar Corporation
[f]Natural and artificial flavor, Virginia Dare, Inc.
[g]Brand of crosslinked carboxymethylcellulose sodium, a product of FMC Corporation, Philadelphia PA, U.S.A.

Formulation 1ASP is characterized as being not sufficiently sweet and possessing a gritty mouthfeel. Formulation 2ASP is characterized as having good initial taste masking properties. Formulation 3ASP is charasterized as being sour, gritty, and slightly chalky.

EXAMPLE 5

Chewable Aspirin Tablets Prepared with 90% Microcrystalline Cellulose Coprocessed with 10% Guar Gum as Excipient Using Microencapsulated Aspirin The same procedures that are described in Example 4 are used to prepare the chewable aspirin tablets of Example 5. In this example the aspirin used is microencapsulated rather than being untreated aspirin powder. These formulations are detailed in Table 5.

TABLE 5

| Formulation | 4ASP (grams) | 5ASP (grams) | 6ASP (grams) | 7ASP (grams) | 8ASP (grams) |
|---|---|---|---|---|---|
| Aspirin[a] | 66.12 | 66.12 | 66.12 | 66.12 | 66.12 |
| Mannitol | 113.88[b] | 79.1[c] | 79.1[c] | 109.88[b] | 77.0[c] |
| Xylitol | | 4.0 | | | 4.0 |
| MCC-GG[d] | 16.0 | 16.0 | 16.0 | 16.0 | 16.0 |
| Compressible sugar[e] | | 33.88 | 33.88 | | 33.88 |
| Flavoring agent[f] | 2.0 | | 4.0 | 6.0 | 2.0 |
| Ac-Di-Sol[g] | 1.0 | | | 1.0 | |
| Magnesium stearate | 1.0 | 1.0 | 1.0 | 1.0 | 1.0 |

[a]Coated aspirin, Eurand America Corporation
[b]Granular mannitol
[c]Mannitol USP
[d]Novagel ® RCN-10, a product of FMC Corp.
[e]Di-Pac ®, a compressible sugar consisting of 97% sucrose and 3% maltodextrin, Amstar Sugar Corporation
[f]Natural and artificial flavor, Virginia Dare, Inc.
[g]Brand of crosslinked carboxymethylcellulose sodium, a product of FMC Corp.

Formulation 4ASP is characterized as having a sweet-sour aftertaste and being gritty. Formulation 5ASP is described as being very good, but slightly gritty whereas Formulation 6ASP is described as being sweet and overall very good. Both Formulations 7ASP and 8ASP are described as having a sweet, pleasant taste.

EXAMPLE 6

Chewable Aspirin Tablets Prepared with 85% Microcrystalline Cellulose Coprocessed with 15% Guar Gum as Excipient The same procedures that are described in Example 4 are used to prepare the chewable aspirin tablets of Example 6. These formulations are detailed in Table 6.

TABLE 6

| Formulation | 9ASP (grams) | 10ASP (grams) | 11ASP (grams) | 12ASP (grams) |
|---|---|---|---|---|
| Aspirin[a] | 81.25 | 65.0 | 65.0 | 65.0 |
| Mannitol | 143.75[b] | 72.0[c] | 78.0[c] | 77.0[c] |
| Xylitol |  | 4.0 | 1.5 | 4.0 |
| MCC-GG agregate[d] | 20.00 | 20.0 | 16.0 | 16.0 |
| Compressible sugar[e] |  | 36.0 |  | 33.88 |
| Sucrose NF[f] |  |  | 34.5 |  |
| Flavoring agent[g] | 2.50 |  | 3.0 | 2.0 |
| CMC[h] | 1.25 | 1.0 |  |  |
| Magnesium stearate | 1.25 | 2.0 | 2.0 | 1.0 |

[a]Aspirin powder, Dow Chemical USA
[b]Granular mannitol
[c]Mannitol USP
[d]Novagel® RCN-15, a product of FMC Corp., Philadelphia PA, U.S.A.
[e]Di-Pac®, a compressible sugar consisting of 97% sucrose and 3% maltodextrin, Amstar Sugar Corporation
[f]Fruit sugar, Domino Sugar Corporation
[g]Natural and artificial flavor, Virginia Dare, Inc.
[h]Ac-Di-Sol® brand of crosslinked carboxymethylcellulose sodium, a product of FMC Corp., Philadelphia PA, U.S.A.

Formulation 9ASP is characterized as being gritty and having an acidic aftertaste. Formulation 10ASP has an acidic taste. Formulation 11ASP has a pleasant, sweet-sour aftertaste. Formulation 12ASP is described as having some acid-sour aftertaste, but having good taste masking and overall being very good.

EXAMPLE 7

Chewable Aspirin Tablets Prepared with 85% Microcrystalline Cellulose Coprocessed with 15% Guar Gum as Excipient Using Microencapsulated Aspirin The same procedures that are used in Example 4 are used to prepare the chewable aspirin tablets of Example 7. In this example the aspirin used is microencapsulated rather than being untreated aspirin powder. These formulations are detailed in Table 7.

TABLE 7

| Formulation | 13ASP (grams) | 14ASP (grams) | 15ASP (grams) | 16ASP (grams) | 17ASP (grams) |
|---|---|---|---|---|---|
| Aspirin[a] | 66.12 | 66.12 | 66.12 | 66.12 | 66.12 |
| Mannitol[b] | 78.0 | 79.1 | 78.0 | 76.5 | 80.1 |
| Xylitol |  |  | 1.5 | 3.5 |  |
| MCC-GG[c] | 16.0 | 16.0 | 16.0 | 16.0 | 16.0 |
| Compressible sugar[d] | 35.88 |  | 33.88 | 33.88 | 33.88 |
| Sucrose NF[e] |  | 33.88 |  |  |  |
| Flavoring agent[f] | 2.0 | 3.0 | 2.5 | 2.0 | 2.0 |
| Lecithin | 1.0 |  |  |  |  |
| Magnesium stearate | 1.0 | 2.0 | 2.0 | 2.0 | 1.0 |

[a]Coated aspirin, Eurand America, Inc.
[b]Mannitol USP
[c]Novagel® RCN-15, a product of FMC Corp.
[d]Di-Pac®, a compressible sugar consisting of 97% sucrose and 3% maltodextrin, Amstar Sugar Corporation
[e]Fruit sugar, Domino Sugar Corporation
[f]Natural and artificial flavor, Virginia Dare, Inc.

Formulation 13ASP is described as having an acidic taste without any sweetness. Formulation 17ASP is described as being successively very sweet, slightly sour, slightly salty, but with smooth mouthfeel.

EXAMPLE 8

Chewable Aspirin Tablets Prepared with 70% Microcrystalline Cellulose Coprocessed with 30% of a Xanthan Gum/Maltodextrin Combination as An Excipient The method of Example 4 is used to prepare the formulations that are detailed in Table 8, except that the microcrystalline cellulose coprocessed with 10% guar gum {Novagel RCN-10} excipient is replaced by 70% microcrystalline cellulose coprocessed with 30% of a combination of xanthan gum and maltodextrin (MCC-XG-MD).

TABLE 8

| Formulation | 18ASP (grams) | 19ASP (grams) |
|---|---|---|
| Aspirin | 65.0[a] | 66.12[b] |
| Mannitol[c] | 72.0 | 72.00 |
| Xylitol | 4.0 | 4.0 |
| MCC-XG-MD[d] | 20.0 | 20.00 |
| Compressible sugar[e] | 36.0 | 34.88 |
| Ac-Di-Sol[f] | 1.0 | 1.0 |
| Magnesium stearate | 2.0 | 2.0 |

[a]Aspirin powder, Dow Chemical USA
[b]Coated aspirin, Eurand America, Inc.
[c]Mannitol USP
[d]70% MCC coprocessed with 30% xanthan gum and maltodextrin
[e]Di-Pac®, a compressible sugar consisting of 97% sucrose and 3% maltodextrin, Amstar Sugar Corporation
[f]Brand of crosslinked carboxymethylcellulose sodium, a product of FMC Corp.

Formulation 19ASP is described as having an acidic taste.

As shown in the above examples, the MCC-GG is significantly improving the palatability of the chewable pharmaceutical tablets. However, its contribution can be negated by improperly balancing the properties of the other ingredients. For example, different samples of sucrose have different amounts of granular character, a fact which reflects either their particular source or their method of isolation. Similarly, anhydrous mannitol and granular mannitol can have opposite effects. Thus, different grades of sweeteners, for example, can modify the amount of grittiness perceived when the tablets are masticated. It can also be seen that the effects of other ingredients, (including various flavorings, disintegrants such as Ac-Di-Sol® modified cellulose gum, and sweetening alcohols such as xylitol) in the chewable formulation can lead to less than satisfactory performance of a specific formulation in spite of the presence of MCC-GG. By carefully selecting these other ingredients, it is possible to prepare chewable pharmaceutical tablets with MCC-GG as an excipient which have excellent mouthfeel, texture, taste and smell. The choice and amounts of these other ingredients is well within the capabilities of one skilled in the art of making chewable pharmaceutical tablets, and is neither an inventive step nor a step requiring skills beyond those ordinarily possessed by one knowledgable in the chewable tablet art.

We claim:

1. A chewable pharmaceutical tablet comprising an active agent and about 2 to about 15 wt % based on the total dry weight of the formulation of coprocessed aggregate particles of 60 to 99 wt % microcrystalline cellulose and the balance to 100 wt % of the aggregate of at least one galactomannan gum.

2. The chewable pharmaceutical tablet of claim 1 wherein said aggregate consists essentially of substantially spheroidal particles having an average size of about 0.1–100 microns.

3. The chewable pharmaceutical tablet of claims 1 or 2 wherein the microcrystalline cellulose comprises 70 to 95 wt % of said aggregate particles.

4. The chewable pharmaceutical tablet of claim 3 wherein said galactomannan gum is guar gum, locust bean gum, cassia gum, tara gum, or a mixture thereof.

5. The chewable pharmaceutical tablet of claim 4 wherein said galactomannan gum is guar gum, locust bean, or a mixture thereof.

6. The chewable pharmaceutical tablet of claim 4 wherein said galactomannan gum is guar gum.

7. The chewable pharmaceutical tablet of claim 1 wherein said active comprises a prescription pharmaceutical.

8. The chewable pharmaceutical tablet of claim 7 wherein said prescription pharmaceutical is an antibiotic or an anticonvulsant.

9. The chewable pharmaceutical tablet of claim 8 wherein said antibiotic is amoxicillin.

10. The chewable pharmaceutical tablet of claim 1 wherein said active is an allergy relief product.

11. The chewable pharmaceutical tablet of claim 1 wherein said active is an analgesic.

12. The chewable pharmaceutical tablet of claim 1 wherein said analgesic is aspirin, acetaminophen, or ibuprofen.

13. The chewable pharmaceutical tablet of claim 1 wherein said active is an antacid with the optional further presence of a gastrointestinal gas suppressant.

14. The chewable pharmaceutical tablet of claim 1 wherein said gas suppressant comprises simethicone.

15. The chewable pharmaceutical tablet of claim 1 wherein said active is an appetite stimulant or suppressant.

16. The chewable pharmaceutical tablet of claim 1 wherein said active is a cold preparation.

17. The chewable pharmaceutical tablet of claim 1 wherein said active is a cough preparation.

18. The chewable pharmaceutical tablet of claim 1 wherein said active is a dietary supplement.

19. The Chewable pharmaceutical tablet of claim 1 wherein said active is a digestive aid.

20. The chewable pharmaceutical tablet of claim 1 wherein said active is a laxative.

21. The chewable pharmaceutical tablet of claim 1 wherein said active is a mineral or minerals.

22. The chewable pharmaceutical tablet of claim 1 wherein said active is a throat lozenge.

23. The chewable pharmaceutical tablet of claim 1 wherein said active is a vitamin or multivitamin.

24. The chewable pharmaceutical tablet of claim 1 wherein the active is a mixture of two or more said OTC actives.

25. The chewable pharmaceutical tablet of claim 1 further comprising a non-coprocessed hydrocolloid which is gum acacia, kappa-carrageenan, tragacanth gum, konjac, xanthan gum, or a mixture thereof, present in 0.1 to 5.0 wt % based upon the total formulation weight.

26. The chewable pharmaceutical tablet of claims 1 or 25 further comprising maltodextrin present in 0.1 to 5.0 wt % based upon the total formulation weight.

* * * * *